(12) United States Patent
Lee et al.

(10) Patent No.: US 9,518,849 B2
(45) Date of Patent: Dec. 13, 2016

(54) ACOUSTIC SENSOR APPARATUS

(71) Applicant: HYUNDAI MOTOR COMPANY, Seoul (KR)

(72) Inventors: Hui Sung Lee, Gunpo-si (KR); Kwang Myung Oh, Daejeon (KR); Sung Jin Sah, Suwon-si (KR); Sung-Min Park, Seoul (KR)

(73) Assignee: HYUNDAI MOTOR COMPANY (KR)

( * ) Notice: Subject to any disclaimer, the term of this patent is extended or adjusted under 35 U.S.C. 154(b) by 0 days.

(21) Appl. No.: 14/928,543

(22) Filed: Oct. 30, 2015

(65) Prior Publication Data

US 2016/0209249 A1    Jul. 21, 2016

(30) Foreign Application Priority Data

Jan. 20, 2015    (KR) .......................... 10-2015-0009315

(51) Int. Cl.
*G01D 11/24*    (2006.01)

(52) U.S. Cl.
CPC .................................. *G01D 11/245* (2013.01)

(58) Field of Classification Search
CPC .............................. G01D 11/24; G01D 11/245
USPC ........................................................... 73/431
See application file for complete search history.

(56) References Cited

U.S. PATENT DOCUMENTS

| | | | | |
|---|---|---|---|---|
| 4,899,591 A | * | 2/1990 | Kibblewhite | B25B 23/1425 29/594 |
| 5,461,923 A | * | 10/1995 | Meisterling | G01L 5/246 73/597 |
| 6,501,211 B1 | * | 12/2002 | Nasrollahzadeh | H01L 41/042 310/317 |
| 6,955,092 B2 | * | 10/2005 | Keener | G01N 19/04 73/40 |
| 7,412,898 B1 | * | 8/2008 | Smith | G01L 5/24 73/761 |
| 7,467,556 B2 | * | 12/2008 | Kibblewhite | F16B 25/10 73/761 |
| 8,024,979 B2 | * | 9/2011 | Clarke | F16B 31/025 73/760 |
| 8,037,772 B2 | * | 10/2011 | Kibblewhite | F16B 31/02 73/761 |
| 8,177,464 B2 | * | 5/2012 | Zendehroud | F16B 31/025 411/8 |
| 8,810,370 B2 | * | 8/2014 | Tillotson | H04Q 9/00 340/10.1 |
| 9,063,069 B2 | * | 6/2015 | Stickel | G01L 5/246 |

(Continued)

FOREIGN PATENT DOCUMENTS

| | | |
|---|---|---|
| JP | 2002-022760 A | 1/2002 |
| JP | 2002-236064 A | 8/2002 |

(Continued)

*Primary Examiner* — Lisa Caputo
*Assistant Examiner* — Jamel Williams
(74) *Attorney, Agent, or Firm* — Brinks Gilson & Lione (57) ABSTRACT

An acoustic sensor apparatus mounted to a medium is disclosed. The acoustic sensor apparatus includes: a sensor unit processing an input acoustic signal; and a housing including a body unit having an accommodation groove in which the sensor unit is accommodated, a cap unit formed to close an opening of the accommodation groove, and a coupling unit formed to mechanically couple the body unit or the cap unit to a medium.

17 Claims, 12 Drawing Sheets

(56) References Cited

U.S. PATENT DOCUMENTS

2009/0206705 A1* 8/2009 Nies ..................... B23K 20/12
                                                      310/361
2013/0147633 A1   6/2013 Sumrall et al.

FOREIGN PATENT DOCUMENTS

| JP | 2002236064 A * | 8/2002 | |
| JP | WO 2014155792 A1 * | 10/2014 | ............ G01M 3/243 |
| KR | 10-2002-0081198 A | 10/2002 | |
| KR | 10-2009-0045545 | 5/2009 | |
| WO | WO 2007024363 A1 * | 3/2007 | ............. B60R 11/02 |

* cited by examiner

ACOUSTIC SENSOR APPARATUS

CROSS-REFERENCE TO RELATED APPLICATION

This application claims the benefit of Korean Patent Application No. 10-2015-0009315, filed on Jan. 20, 2015, which is hereby incorporated by reference in its entirety.

FIELD

Forms of the present disclosure relate to an acoustic sensor apparatus, and more particularly to an acoustic sensor apparatus mounted to a medium.

BACKGROUND

The statements in this section merely provide background information related to the present disclosure and may not constitute prior art.

An acoustic sensor configured to obtain necessary information using acoustic waves includes a housing for protecting the acoustic sensor from external impact and pollutants. Conventionally, an adhesive or an adhesive tape has been used to mount the housing of the acoustic sensor to a target object.

However, if the acoustic sensor is attached to the target object using adhesive force, adhesive force of the attached part between the acoustic sensor and the target object is deteriorated by peripheral pollutants, environmental factors (e.g., temperature, humidity, etc.), or the passage of time. In addition, an unexpected deviation may occur in adhesive strength and installation position of the acoustic sensor according to dexterity of a user who attaches the acoustic sensor, such that such deviation may disturb transmission of correct acoustic waves. In addition, the attached part must be removed for maintenance of the acoustic sensor and the user may have difficulty in re-installation of the acoustic sensor.

Korean Patent Publication No. 10-1999-0073787 (published on Oct. 5, 1999) has disclosed a vehicle speed sensor configured to correctly calculate a vehicle speed while a vehicle runs at a low speed using the acoustic sensor.

SUMMARY

The present disclosure provides an acoustic sensor apparatus which can be standardized in terms of operation without using adhesive and can also be strongly fixed to a medium, such that a housing for protecting a membrane can be fixed to the medium.

Additional aspects of the present disclosure will be set forth in part in the description which follows and, in part, will be obvious from the description, or may be learned by practice of the present disclosure.

In accordance with another aspect of the present disclosure, an acoustic sensor apparatus includes: a sensor unit configured to process an input acoustic signal; and a housing including a body unit having an accommodation groove in which the sensor unit is accommodated, a cap unit formed to close an opening of the accommodation groove, and a coupling unit formed to mechanically couple the body unit or the cap unit to a medium.

The coupling unit may include any one of a bolt, a screw, and a rivet.

The coupling unit may be configured to mechanically couple a first medium to a second medium.

The sensor unit may include an input unit configured to receive an acoustic signal; and a vibration space in which air vibrates by vibration of the housing may be formed in the vicinity of the input unit.

The acoustic sensor apparatus may further include a connection unit configured to electrically couple the sensor unit to an external part.

The connection unit may be formed to pass through the housing, and one side of the connection unit may be electrically coupled to the sensor unit and the other side thereof may be exposed to outside.

The sensor unit may further include: an input unit configured to receive an acoustic signal; a circuit unit configured to process an output signal of the input unit; and a substrate, one surface of which is connected to the input unit and the circuit unit and the other surface of which is electrically coupled to the external part.

One surface of the substrate may be spaced apart from the accommodation groove, and a vibration space in which air vibrates by vibration of the housing may be formed in the vicinity of the input unit.

The sensor unit may further include: an input unit configured to receive an acoustic signal; a circuit unit configured to process an output signal of the input unit; and a substrate, one surface of which is connected to the input unit, the circuit unit, and the connection unit, wherein one surface of the substrate is spaced apart from the cap unit, and a vibration space in which air vibrates by vibration of the housing is formed in the vicinity of the input unit.

The substrate may be seated on the bottom surface of the accommodation groove.

The connection unit may include a space concaved inward at one surface contacting the substrate, and at least one of the input unit and the circuit unit may be accommodated in the concaved space of the connection unit.

The sensor unit may include an input unit configured to receive an acoustic signal, and a vibration space in which air vibrates may be formed in the vicinity of the input unit; and the housing may include an air introduction hole through which the vibration space communicates with an external part.

The sensor unit may include an input unit configured to receive an acoustic signal, and a vibration space in which air vibrates may be formed in the vicinity of the input unit; the housing may include an air introduction hole through which the vibration space communicates with an external part; and the connection unit may be exposed to outside through the air introduction hole.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the following description of the present disclosure, a detailed description of known functions and configurations incorporated herein will be omitted when it may make the subject matter of the present disclosure rather unclear. In the drawings, elements unrelated to the forms of the present disclosure are omitted for clarity and the size of the components may be exaggerated for easy understanding.

An acoustic sensor apparatus 100 according to one form can perform a specific function by sensing or detecting acoustic waves. Alternatively, the acoustic sensor apparatus 100 analyzes a waveform of acoustic waves, so that it may inform a user of information associated with the analyzed result or may implement a variety of functions according to various waveforms.

On the other hand, the acoustic sensor apparatus 100 according to the form may be mounted to various media 10. For example, the acoustic sensor apparatus 100 may be mounted to a vehicle. The vehicle including the acoustic sensor apparatus 100 may recognize a voice signal of a user and perform a command corresponding to the recognized voice signal, or may recognize an external acoustic signal and perform a specific function corresponding to the recognized acoustic signal. Alternatively, the vehicle including the acoustic sensor apparatus 100 may recognize vibration generated by finger touching or tapping and thus perform a specific function corresponding to the recognized vibration.

Figure 1:
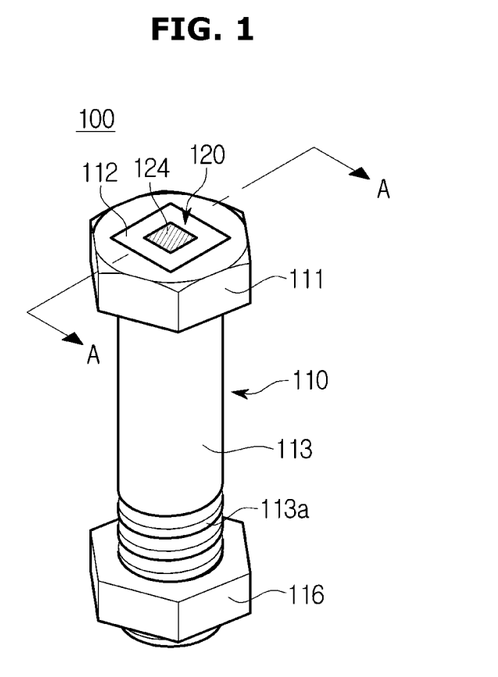
FIG. 1 is a perspective view illustrating an acoustic sensor apparatus according to a first form of the present disclosure.
Figure 2:
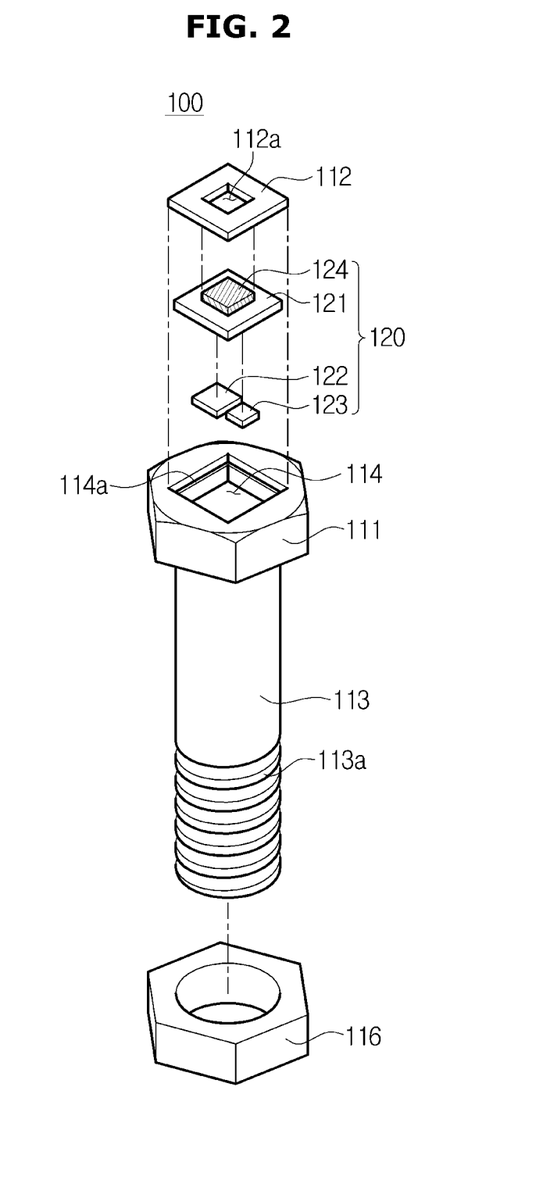
FIG. 2 is an exploded perspective view illustrating the acoustic sensor apparatus shown in FIG. 1.
Figure 3:
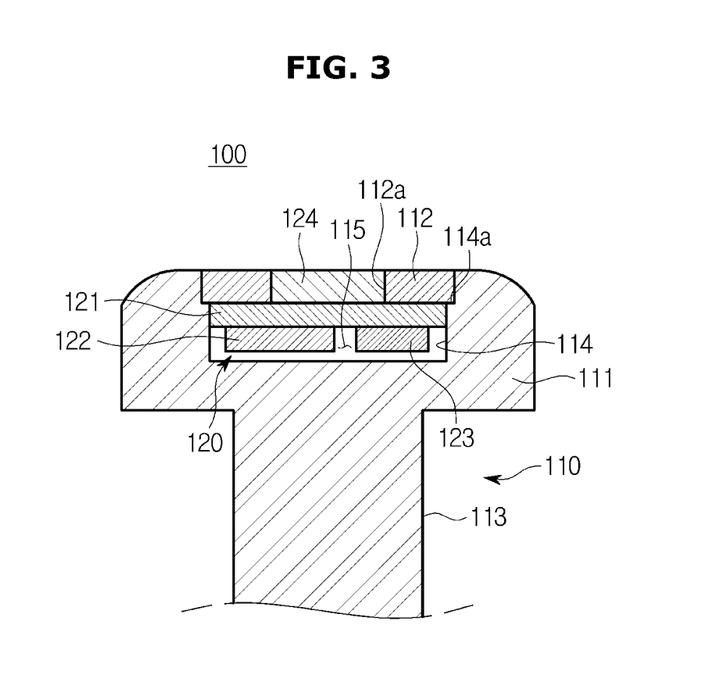
FIG. 3 is a cross-sectional view illustrating the acoustic sensor apparatus taken along the line A-A of FIG. 1.

The acoustic sensor apparatus 100 according to a first form of the present disclosure will hereinafter be described with reference to FIGS. 1 to 3. FIG. 1 is a perspective view illustrating an acoustic sensor apparatus according to a first form of the present disclosure. FIG. 2 is an exploded perspective view illustrating the acoustic sensor apparatus shown in FIG. 1. FIG. 3 is a cross-sectional view illustrating the acoustic sensor apparatus taken along the line A-A of FIG. 1.

The acoustic sensor apparatus 100 according to the first form may include a sensor unit 120 for receiving and processing an acoustic signal; and a housing 110 for supporting the sensor unit 120.

The sensor unit 120 may include an input unit 122 configured to receive an acoustic signal; a circuit unit 123 configured to process a signal received from the input unit 122; and a substrate 121 connected to the input unit 122 and the circuit unit 123.

For example, the input unit 122 may be implemented as a membrane vibrated by acoustic waves. The input unit 122 may be electrically connected to the substrate 121, and may convert vibration of the membrane into an electrical signal. Meanwhile, the input unit 122 may also be implemented by any one of all kinds of units capable of converting acoustic waves into an electrical signal and transmitting the electrical signal.

For example, the circuit unit 123 may be implemented as application specific integrated circuit (ASIC). The circuit unit 123 may be electrically connected to the substrate 121, and may process signals received from the input unit 122. The signals received from the input unit 122 may be ON/OFF signals based on the presence or absence of acoustic waves, or may be consecutive signals changed according to a waveform of the acoustic waves.

The substrate 121 may be a printed circuit board (PCB). The substrate 121 may support the input unit 122 and the circuit unit 123. For example, the input unit 122 and the circuit unit 123 may be mounted to one surface of the substrate 121. Meanwhile, the circuit unit 123 may be incorporated with the substrate 121.

In addition, the substrate 121 may include a line (or a wire) configured to form a circuit. The input unit 122 may be electrically connected to the line of the substrate 121 so that it converts the acoustic signal into an electrical signal and transmits the electrical signal. The circuit unit 123 may be electrically connected to the line of the substrate 121 so that it can analyze and process the electrical signal received from the input unit 122.

The sensor unit 120 may further include a connection unit 124. The connection unit 124 electrically connects the substrate 121 to an external part so that it can transmit not only information regarding acoustic waves received from the input unit 122 but also information processed by the circuit unit 123 to the external part. Here, the external part may be an electronic control unit (ECU) of a vehicle.

The connection unit 124 shown in FIGS. 1 to 3 may be a connector, one side of which is electrically connected to the substrate 121 and the other side of which is exposed to the outer surface of the housing 110. The connector may be formed of a conductive material, for example, a metal such as copper (Cu).

The housing 110 may include a body unit 111 in which an accommodation groove 114 including the sensor unit 120 is formed; a cap unit 112 configured to close an opening of the accommodation groove 114; and a coupling unit 113 configured to mechanically couple the body unit 111 to the medium 10.

The body unit 111 may include the accommodation groove 114 that is concaved at one surface of the body unit 111. The accommodation groove 114 may include the sensor unit 120 therein. The cap unit 112 may be configured to cover the opening of the body unit 111. In this case, the cap unit 112 may seal the sensor unit 120 from the external part, or may include a space formed to communicate with the external part. Meanwhile, the accommodation groove 114 may be formed in the cap unit 112, and may also be simultaneously formed in the body unit 111 and the cap unit 112.

The body unit 111 and the cap unit 112 may block the sensor unit 112 from the external part. That is, the body unit 111 and the cap unit 112 may protect the sensor unit 120 from external impact or pollutants. The above-mentioned operation for blocking the sensor unit 120 from the external part may conceptually include not only sealing but also enclosing the circumference of the sensor unit 120 so that it can prevent external access.

The substrate 121 may be fixed to one surface of the cap unit 112. In this case, the fixing method between the substrate 121 and the cap unit 112 may include a mechanical coupling method or an adhesive method. The input unit 122 and the circuit unit 123 may be fixed to one surface of the substrate 121. Therefore, the input unit 122 and the circuit unit 123 may be fixed to one surface of the substrate 121, and the cap unit 112 may be fixed to the other surface of the substrate 121. Here, the input unit 122 and the circuit unit 123 may be electrically connected to the substrate 121.

The cap unit 112 may include a connection-part accommodation hole 112a through which the connection unit 124 passes 124. One side of the connection unit 124 may be electrically connected to the substrate 121, and the other side of the connection unit 124 may be exposed to the outer surface of the cap unit 112. That is, the connection unit 124 may pass through the connection-part accommodation hole 112a formed in the cap unit 112. The exposed surface of the connection unit 124 is connected to a cable or the like, such that the connection unit 124 may be electrically connected to an ECU or the like.

A support projection 114a for supporting the cap unit 112 may be formed at the outer side of the accommodation groove 114 of the body unit 111. The cap unit 112 supported by the support projection 114a may be fixed to the body unit 111. The fixing method between the cap unit 112 and the body unit 111 may include a mechanical coupling method or an adhesive method.

The input unit 122 may be spaced apart from the accommodation groove 114 of the body unit 111, such that a vibration space 115 may be formed between the accommodation groove 114 and the input unit 122. If the housing 110 vibrates by external vibration or impact, the air contained in the vibration space 115 vibrates, and the input unit 122 configured to receive vibration of the air contained in the vibration space 115 may output a signal. For example, vibration of the air contained in the vibration space 115 may cause vibration of the membrane of the input unit 122, and such vibration of the membrane may cause variation of a current, such that the membrane can output an electrical signal on the basis of such current variation.

For example, the substrate 121, the input unit 122, and the circuit unit 123 may be supported by the cap unit 112, resulting in formation of one structure. Under the condition that the cap unit 112 is supported by the support projection 114a, one surface of the input unit 122 may be spaced apart from an inner surface of the accommodation groove 114. Therefore, a vibration space 115 in which the air generated by vibration of the body unit 111 is accommodated may be formed between the input unit 122 and the accommodation groove 114.

The coupling unit 113 will hereinafter be described with reference to FIGS. 4 and 5.

Figure 4:
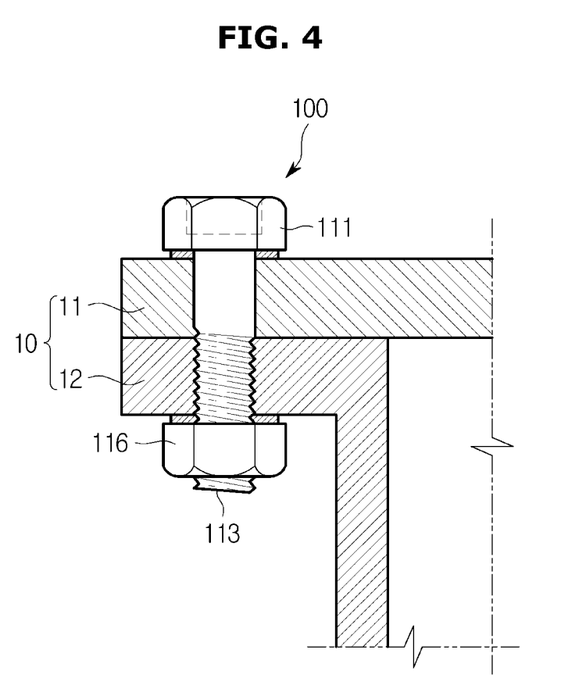
FIG. 4 is a cross-sectional view illustrating exemplary installation of an acoustic sensor apparatus according to a first form of the present disclosure.

FIG. 4 is a cross-sectional view illustrating exemplary installation of an acoustic sensor apparatus 100 according to a first form of the present disclosure. FIG. 5 is a cross-sectional view illustrating exemplary installation of an acoustic sensor apparatus 100-1 according to a modified form of FIG. 4.

A thread 113a may be formed at the outer surface of the coupling unit 113. In addition, the coupling unit 113 may be formed in various shapes through which the coupling unit 113 can be mechanically coupled to the medium 10 (11, 12). For example, the coupling unit 113 may be in the form of a screw, a bolt, or a rivet. Although the coupling unit 113 protruding from the body unit 111 is shown in FIGS. 4 and 5, the coupling unit 113 may include a concave portion formed in the body unit 111. For example, the coupling unit 113 may be a nut in which one side is opened and a thread is formed at the inner circumference.

Referring to FIG. 4, the housing 110 may mechanically couple a first medium 11 to a second medium 12. The coupling unit 113 may be a bolt coupled to a hole that passes through the first medium 11 and the second medium 12.

A coupling counterpart 116 is combined with the coupling unit 113 protruded outward from the second medium 12, such that the coupling counterpart 116 can be strongly locked to the first medium 11 and the second medium 12. In this case, the coupling counterpart 116 may be a nut combined with the thread 113a of the outer surface of the coupling unit 113.

On the other hand, the housing 110 according to the first form may couple the first medium 11 to the second medium 12, or may also fix the sensor unit 120 to the medium 10. That is, instead of attaching the sensor unit 120 to the medium 10, the coupling unit 113 is mechanically coupled to the medium 10 such that the sensor unit 120 can be fixed to the medium 10.

Figure 5:
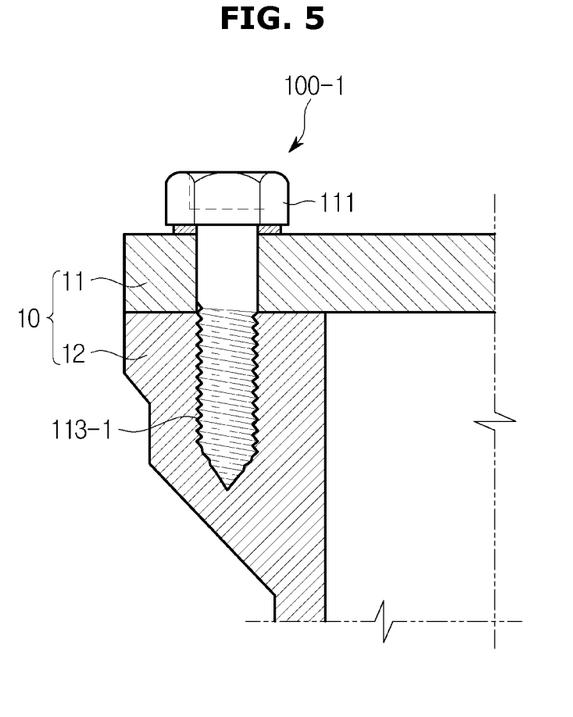
FIG. 5 is a cross-sectional view illustrating exemplary installation of an acoustic sensor apparatus according to a modified form of FIG. 4.

Referring to FIG. 5, the coupling unit 113-1 may pass through the first medium 11 so that the coupling unit 113-1 may be screwed onto the second medium 12. As described above, the housing 110-1 may interconnect the first medium 11 and the second medium 12, and at the same time may fix the sensor unit 120 to the medium 10. Although not shown in FIG. 5, it should be noted that the coupling unit 113 can be coupled to the first medium 11 only. In addition, the coupling unit 113-1 may be a rivet.

Figure 6:
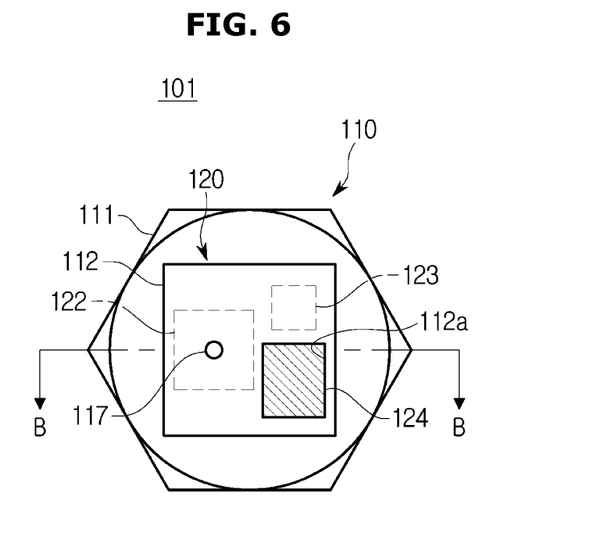
FIG. 6 is a perspective view illustrating an acoustic sensor apparatus according to a second form of the present disclosure.
Figure 7:
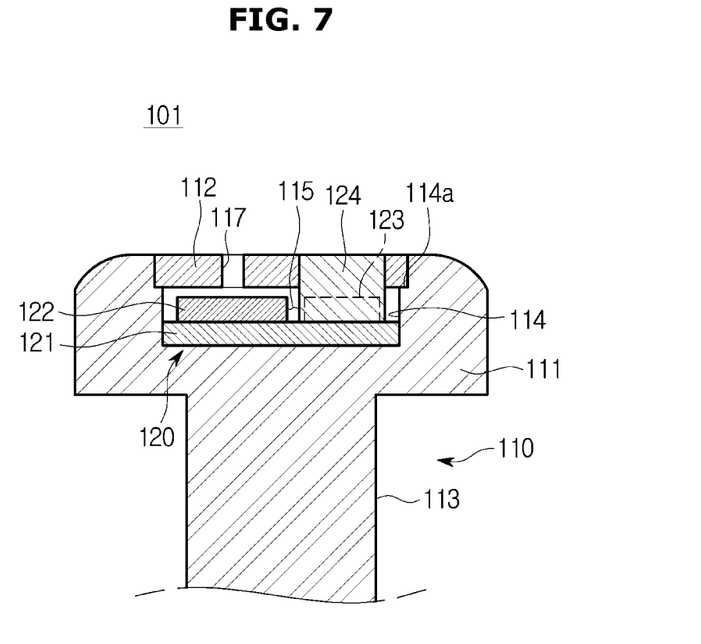
FIG. 7 is a cross-sectional view illustrating the acoustic sensor apparatus taken along the line B-B of FIG. 6.

An acoustic sensor apparatus 101 according to a second form of the present disclosure will hereinafter be described with reference to FIGS. 6 and 7. FIG. 6 is a perspective view illustrating an acoustic sensor apparatus 101 according to a second form of the present disclosure. FIG. 7 is a cross-sectional view illustrating the acoustic sensor apparatus taken along the line B-B of FIG. 6.

Referring to FIG. 7, the bottom surface of the substrate 121 of the acoustic sensor apparatus 101 according to the second form of the present disclosure may be seated and fixed to the bottom surface of the accommodation groove 114. The input unit 122 and the circuit unit 123 of the sensor unit 120 may be electrically coupled to the top surface of the substrate 121. One surface of the connection unit 124 may be connected to the top surface of the substrate 121, and the other surface of the connection unit 124 may pass through the cap unit 112 and may be exposed to the outside.

The input unit 122 may be spaced apart from the cap unit 112. For example, one surface of the input unit 122 may be spaced apart from the bottom surface of the cap unit 112 under the condition that the cap unit 112 is supported by the support projection 114a formed in the accommodation groove 114. Therefore, a vibration space 115 in which the air generated by vibration of the body unit 111 can be accommodated may be formed between the input unit 122 and the cap unit 112.

The cap unit 112 may include an air introduction hole 117 through which the vibration space 115 communicates with the external part or outside. The air introduction hole 117 may be arranged over the input unit 122. In one form, the air introduction hole 117 may be formed at the position corresponding to the center part of the input unit 122. The acoustic waves received through the air introduction hole 117 may vibrate the air contained in the vibration space 115, and the input unit 122 may convert vibration of the air contained in the vibration space 115 and output an output signal according to the conversion result.

Meanwhile, the acoustic sensor apparatus 101 according to the second form may directly receive the acoustic waves through the air introduction hole 117. That is, the acoustic sensor apparatus 101 can more precisely analyze the acoustic waves as compared to the case in which vibration of the housing 110 is used as an input signal. Therefore, it is possible to output different output signals according to waveforms of the acoustic waves. In addition, the input signal of the housing 110 vibrated by external vibration or impact may be output as the output signal as necessary.

Figure 8:
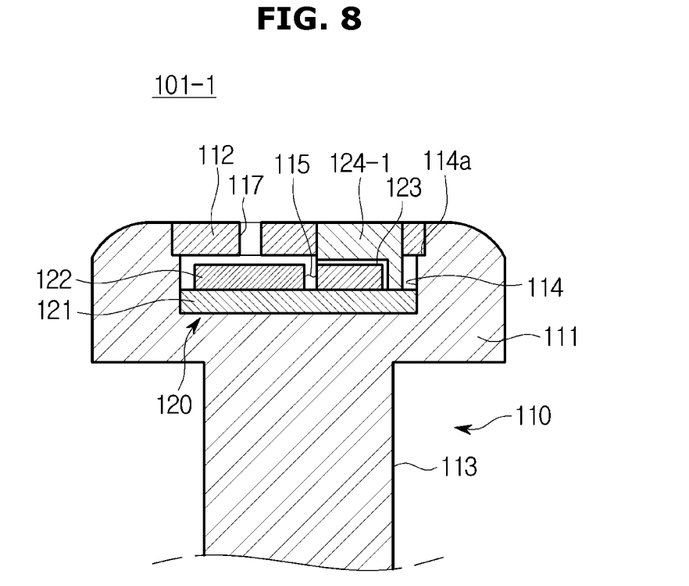
FIG. 8 is a cross-sectional view illustrating an acoustic sensor apparatus according to a modified form of FIG. 7.

FIG. 8 is a cross-sectional view illustrating an acoustic sensor apparatus according to a modified form of FIG. 7.

Referring to FIG. 8, the connection unit 124 of the acoustic sensor apparatus 101-1 may include a groove in which the input unit 122 or the circuit unit 123 can be accommodated. Since the substrate 121 has a limited width, if the input unit 122, the circuit unit 123, and the connection unit 124 are arranged at one surface of the substrate 121, there is a limitation in size of individual units (122, 123, 124). In this case, as can be seen from FIG. 8, if one side of the connection unit 124 coupled to the substrate 121 is concaved to form a space, the input unit 122 or the circuit unit 123 may be contained in the space, such that the input unit 122 or the circuit unit 123 may have an increased degree of freedom in arrangement and size. In addition, since a necessary width of the connection unit 124 exposed through the cap unit 112 can be maintained, no problem occurs in connection to the external part.

Figure 9:
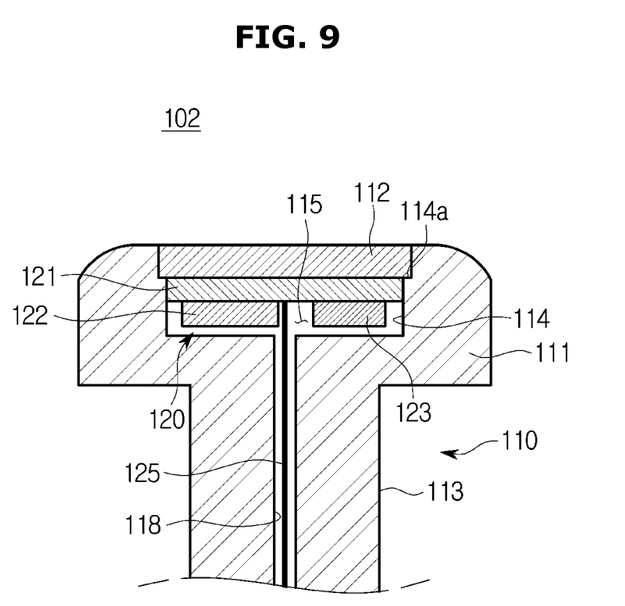
FIG. 9 is a cross-sectional view illustrating an acoustic sensor apparatus according to a third form of the present disclosure.

FIG. 9 is a cross-sectional view illustrating an acoustic sensor apparatus 102 according to a third form of the present disclosure.

Referring to FIG. 9, the connection unit may be a cable 125 electrically coupled to the substrate 121. Meanwhile, the housing 110 may include a connection-part accommodation hole 118 formed to accommodate the cable 125 therein.

The connection-part accommodation hole 118 may be formed to pass through the body unit 111 or the coupling unit 113. In FIG. 9, the connection-part accommodation hole 118 communicating with the external part may start from the bottom part of the accommodation groove 114 and may pass through the body part 111 and the coupling unit 113. In addition, a cable-shaped connection unit 125 may be connected to the external part along the connection-part accommodation hole 118.

Figure 10:
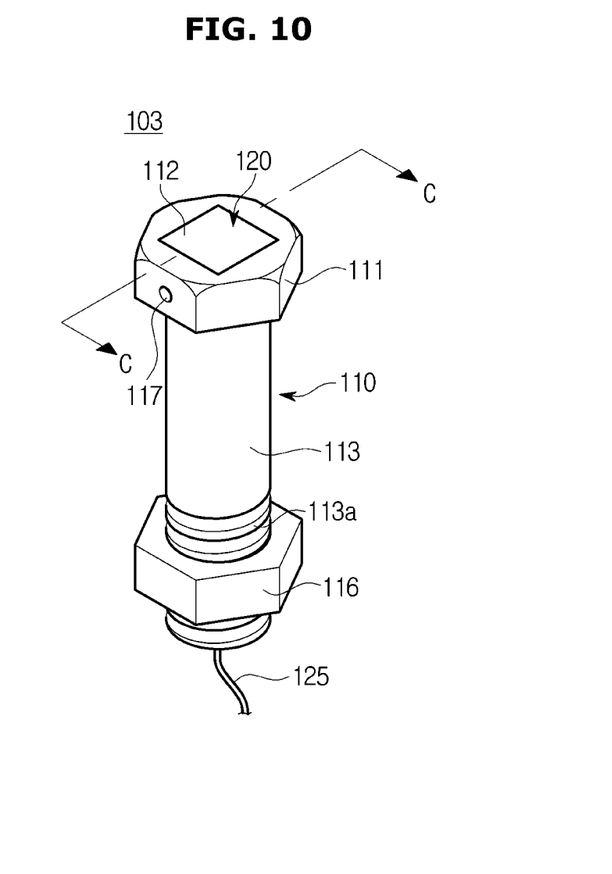
FIG. 10 is a perspective view illustrating an acoustic sensor apparatus according to a fourth form of the present disclosure.
Figure 11:
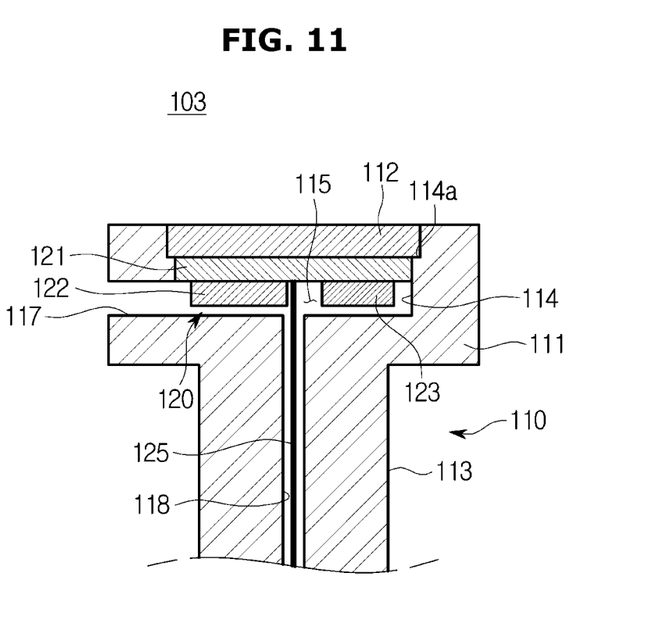
FIG. 11 is a cross-sectional view illustrating the acoustic sensor apparatus taken along the line C-C of FIG. 10.

FIG. 10 is a perspective view illustrating an acoustic sensor apparatus 102 according to a fourth form of the present disclosure. FIG. 11 is a cross-sectional view illustrating the acoustic sensor apparatus taken along the line C-C of FIG. 10.

Referring to FIGS. 10 and 11, the air introduction hole 117 through which the vibration space 115 communicates with the external part may be formed to pass through the housing 110.

One surface of the substrate 121 is fixed to the cap unit 112, and the input unit 122 and the circuit unit 123 may be installed at the other surface of the substrate 121. In this case, the input unit 122 may be spaced from the bottom surface of the accommodation groove 114, and the vibration space 115 may be formed in the vicinity of the input unit 122.

Meanwhile, the air introduction hole 117 communicating with the accommodation groove 114 may be formed at the outside of the body unit 111. The air introduction hole 117 is formed to communicate with the vibration space 115, and external acoustic waves may be directly input to the input unit 122.

The air introduction hole 117 may be provided at the outside of the body unit 111 so that the amount of received external pollutants can be minimized.

Figure 12:
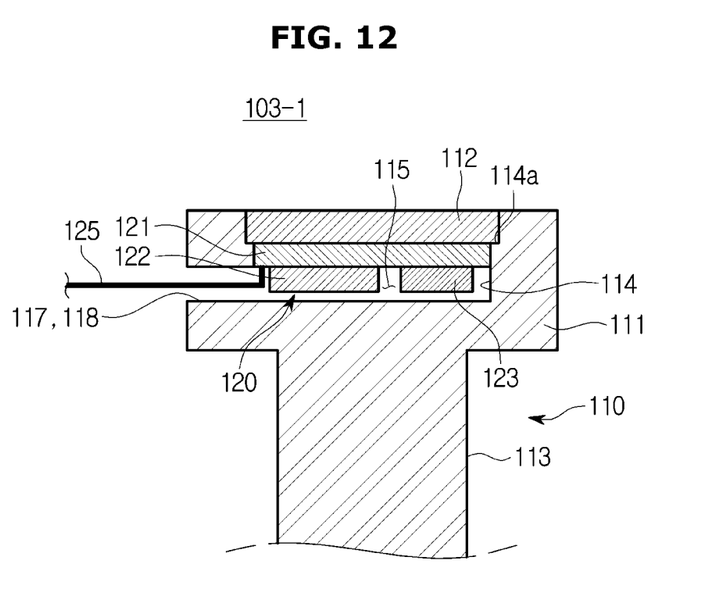
FIG. 12 is a cross-sectional view illustrating the acoustic sensor apparatus according to a modified form of the present disclosure.

FIG. 12 is a cross-sectional view illustrating the acoustic sensor apparatus according to a modified form of the present disclosure.

In the acoustic sensor apparatus 103-1 shown in FIG. 12, the air introduction hole 117 and the connection-part accommodation hole 118 may be integrated with each other. That is, the cable-shaped connection unit 125 may be connected to the external part through the air introduction hole 117. Therefore, the connection-part accommodation hole 118 need not be additionally installed.

As is apparent from the above description, the acoustic sensor apparatus according to the forms is mechanically combined with a medium, so that the acoustic sensor apparatus can be strongly combined with the medium.

In addition, the installation process of the acoustic sensor apparatus can be standardized so that the accurate installation process is achieved even when an operator who performs the installation process is changed to another operator. Therefore, the acoustic sensor apparatus can provide uniform performance for each product.

In addition, the acoustic sensor apparatus can be detached from the medium by releasing a combination unit mechanically combined with the acoustic sensor apparatus, such that maintenance of the acoustic sensor apparatus can be facilitated and time and costs consumed for reinstallation of the acoustic sensor apparatus can be greatly reduced.

Although a few forms of the present disclosure have been shown and described, it would be appreciated by those skilled in the art that changes may be made in these forms without departing from the principles and spirit of the present disclosure, the scope of which is defined in the claims and their equivalents.

What is claimed is:
1. An acoustic sensor apparatus comprising:
a sensor unit configured to process an input acoustic signal; and
a housing comprising:
a body unit having an accommodation groove in which the sensor unit is accommodated,
a cap unit formed to close an opening of the accommodation groove, and
a coupling unit configured to mechanically couple the body unit or the cap unit to a medium,
wherein one surface of the sensor unit is spaced apart from the accommodation groove and a vibration space in which air vibrates by vibration of the housing is formed in the vicinity of the sensor unit.
2. The acoustic sensor apparatus according to claim 1, wherein the coupling unit comprises any one of a bolt, a screw, and a rivet.

3. The acoustic sensor apparatus according to claim 2, wherein the coupling unit is configured to mechanically couple a first medium to a second medium.

4. The acoustic sensor apparatus according to claim 1, wherein the sensor unit comprises an input unit configured to receive an acoustic signal
the vibration space is formed in a vicinity of the input unit.

5. The acoustic sensor apparatus according to claim 1, further comprising:
a connection unit configured to electrically couple the sensor unit to an external part.

6. The acoustic sensor apparatus according to claim 5, wherein one side of the connection unit is electrically coupled to the sensor unit and other side thereof is exposed to outside of the housing.

7. The acoustic sensor apparatus according to claim 6, wherein the sensor unit further comprises:
an input unit configured to receive an acoustic signal;
a circuit unit configured to process an output signal of the input unit; and
a substrate, one surface of which is connected to the input unit, the circuit unit, and the connection unit,
wherein one surface of the substrate is spaced apart from the cap unit, and the vibration space is formed in a vicinity of the input unit.

8. The acoustic sensor apparatus according to claim 6, wherein the sensor unit comprises an input unit configured to receive an acoustic signal, and the vibration space formed in a vicinity of the input unit, the housing comprising an air introduction hole through which the vibration space communicates with an external part, and the connection unit being exposed to outside through the air introduction hole.

9. The acoustic sensor apparatus according to claim 1, wherein the sensor unit further comprises:
an input unit configured to receive an acoustic signal;
a circuit unit configured to process an output signal of the input unit; and
a substrate, one surface of which is connected to the input unit and the circuit unit and another surface of which is electrically coupled to an external part.

10. The acoustic sensor apparatus according to claim 9, wherein
one surface of the substrate is spaced apart from the accommodation groove, and the vibration space is formed in a vicinity of the input unit.

11. The acoustic sensor apparatus according to claim 10, wherein the substrate is seated on the bottom surface of the accommodation groove.

12. The acoustic sensor apparatus according to claim 1, wherein the sensor unit comprises an input unit configured to receive an acoustic signal, and the vibration space formed in a vicinity of the input unit; and
the housing includes an air introduction hole through which the vibration space communicates with an external part.

13. An acoustic sensor apparatus, comprising:
a sensor unit configured to process an acoustic signal;
a housing comprising a housing portion and a coupling portion configured to connect the housing portion to a medium, an inner surface of the housing portion forming an opening configured to accommodate the sensor unit; and
a cap unit configured to close the opening,
wherein a part of the inner surface of the housing portion is spaced apart from the sensor unit or the cap unit, forming a vibration space in which air vibrates by vibration of the housing, and the vibration space formed in the vicinity of the sensor unit.

14. The acoustic sensor apparatus according to claim 13, wherein the sensor unit comprises:
an input unit configured to receive the acoustic signal;
a circuit unit configured to process an output signal of the input unit; and
a substrate connected to the input unit, the circuit unit, the substrate electrically coupled to an external part.

15. An acoustic sensor apparatus comprising:
a sensor unit configured to process an input acoustic signal; and
a housing comprising:
a body unit having an accommodation groove in which the sensor unit is accommodated,
a cap unit formed to close an opening of the accommodation groove, and
a coupling unit configured to mechanically couple the body unit or the cap unit to a medium,
wherein the sensor unit further comprises:
an input unit configured to receive an acoustic signal,
a circuit unit configured to process an output signal of the input unit, and
a substrate, one surface of which is connected to the input unit and the circuit unit and another surface of which is electrically coupled to an external part,
wherein one surface of the substrate is spaced apart from the accommodation groove, and a vibration space in which air vibrates by vibration of the housing is formed in a vicinity of the input unit,
wherein the substrate is seated on a bottom surface of the accommodation groove, a connection unit electrically coupled to the sensor unit comprises a space concaved inward at one surface contacting the substrate, and at least one of the input unit or the circuit unit is accommodated in the concaved space of the connection unit.

16. The acoustic sensor apparatus according to claim 15, wherein the housing comprises an air introduction hole through which the vibration space communicates with an external part.

17. The acoustic sensor apparatus according to claim 16, wherein the connection unit is exposed to outside through the air introduction hole.

\* \* \* \* \*